— US006165476A

United States Patent [19]
Strom et al.

[11] Patent Number: 6,165,476
[45] Date of Patent: Dec. 26, 2000

[54] FUSION PROTEINS WITH AN IMMUNOGLOBULIN HINGE REGION LINKER

[75] Inventors: Terry B. Strom; Xin Xiao Zhen, both of Brookline, Mass.

[73] Assignee: Beth Israel Deaconess Medical Center, Boston, Mass.

[21] Appl. No.: 08/891,271

[22] Filed: Jul. 10, 1997

[51] Int. Cl.[7] .................. C07H 21/00; C07K 14/455; C07K 19/00

[52] U.S. Cl. ................ 424/195.11; 424/85.2; 435/69.7; 435/325; 435/252.3; 435/320.1; 530/351; 530/387.3; 530/399; 536/23.4

[58] Field of Search .................. 530/351, 387.3, 530/399; 435/69.7, 325, 252.3, 320.1; 424/85.1, 85.2, 192.1, 198.1, 93.2; 536/23.4; 935/10

[56] References Cited

U.S. PATENT DOCUMENTS

| | | | |
|---|---|---|---|
| 4,816,567 | 3/1989 | Cabilly et al. | 530/387 |
| 4,874,813 | 10/1989 | O'Shannessy | 525/54.1 |
| 5,073,627 | 12/1991 | Curtis et al. | 530/351 |
| 5,091,513 | 2/1992 | Huston et al. | 530/387 |
| 5,114,711 | 5/1992 | Bell et al. | 424/85.1 |
| 5,116,964 | 5/1992 | Capon et al. | 536/27 |
| 5,225,538 | 7/1993 | Capon et al. | 530/387.3 |
| 5,314,995 | 5/1994 | Fell, Jr. et al. | 530/351 |
| 5,349,053 | 9/1994 | Landolfi | 530/351 |
| 5,428,130 | 6/1995 | Capon et al. | 530/350 |
| 5,547,852 | 8/1996 | Seiler et al. | 435/29 |
| 5,580,853 | 12/1996 | Sytkowski | 514/8 |
| 5,614,184 | 3/1997 | Sytkowski et al. | 424/85.1 |
| 5,672,683 | 9/1997 | Friden et al. | 530/350 |
| 5,738,849 | 4/1998 | Bauer et al. | 424/192.1 |
| 5,759,536 | 6/1998 | Bellgrau et al. | 424/93.21 |

FOREIGN PATENT DOCUMENTS

| | | |
|---|---|---|
| 79357/91 | 6/1991 | Australia . |
| 0 283 244 B1 | 3/1988 | European Pat. Off. . |
| 0 464 533 B1 | 6/1991 | European Pat. Off. . |
| 464 533 A1 | 6/1991 | European Pat. Off. . |
| 0 622 459 A1 | 4/1994 | European Pat. Off. . |
| 0618227A1 | 5/1994 | European Pat. Off. . |
| 0 816 510 A1 | 12/1996 | European Pat. Off. . |
| WO 91/19739 | 12/1991 | WIPO . |
| WO 92/06116 | 4/1992 | WIPO . |
| WO 92/06117 | 4/1992 | WIPO . |
| WO 94/02611 | 2/1994 | WIPO . |
| WO 94/09817 | 5/1994 | WIPO . |
| WO 94/13806 | 6/1994 | WIPO . |
| WO 95/02421 | 1/1995 | WIPO . |
| WO 95/25746 | 9/1995 | WIPO . |
| WO 95/33057 | 12/1995 | WIPO . |
| WO 96/19573 | 6/1996 | WIPO . |
| WO 97/00319 | 1/1997 | WIPO . |
| WO 97/12985 | 4/1997 | WIPO . |

OTHER PUBLICATIONS

R. Callard et al., eds. "The Cytokine FactsBook", pp. 41–42. Academic Press, San Diego, 1994.

M.E. Shapiro et al., "In vivo Studies with Chimeric Toxins: Interleukin–2 Fusion Toxins as Immunosuppressive Agents" Targeted Diagn. Ther. 7:383, 1992.

Jelkmann, W., "Biology of erythropoietin", *Clin. Investig.* 72:S3–S10 (1994).

Yamaguchi, K., et al., "Effects of Site–directed Removal of N–Glycosylation Sites in Human Erythropoietin on Its Production and Biological Properties," *J. Biol. Chem.,* 266(30):20434–20439 (1991).

Boissel, J.P. and Bunn, H.F., "Erythropoietin Structure–Function Relationships," In *The Biology of Hematopoiesis,* (Wiley–Liss, Inc.), pp. 227–232 (1990).

Dubé, S., et al., "Glycosylation at Specific Sites of Erythropoietin Is Essential for Biosynthesis, Secretion, and Biological Function," *J. Biol. Chem.,* 263(33):17516–17521 (1988).

Wen, D., et al., "Erythropoietin Structure–Function Relationships: High Degree of Sequence Homology Among Mammals," *Blood,* 82(5):1507–1516 (1993).

Wen, D., et al., "Erythropoietin Structure–Function Relationships: Identification of Functionally Important Domains," *J. Biol. Chem.,* 269(36):22839–22846 (1994).

Boissel, J–P., et al., "Erythropoietin Structure–Function Relationships: Mutant Proteins That Test A Model of Tertiary Structure," *J. Biol. Chem.,* 268(21):15983–15993 (1993).

Chern, Y., et al., "Potentiation of the Erythropoietin Response by Dimethyl Sulfoxide Priming of Erythroleukemia Cells: Evidence for Interaction of Two Signaling Pathways," *Blood,* 76(11):2204–2209 (1990).

Sytkowski, A., et al., "Immunochemical Studies of Human Erythropoietin Using Site–Specific Anti–peptide Antibodies: Identification of a Functional Domain," *J. Biol. Chem.,* 262(3):1161–1165 (1987).

Sytkowski, A., et al., "Isolation and Characterization of an Anti–Peptide Monoclonal Antibody to Human Erythropoietin," *J. Biol. Chem.,* 260(27):14727–14731 (1985).

Feldman, L., et al., "Four Unique Monoclonal Antibodies to the Putative Receptor Binding Domain of Erythropoietin Inhibit the Biological Function of the Hormone," *Exp. Hematol.,* 20:64–68 (1992).

Fibi, M.R., et al., "N–and O–Glycosylation Muteins of Recombinant Human Erythropoietin Secreted from BHK–21 Cells," *Blood,* 85(5):1229–1236 (1995).

(List continued on next page.)

*Primary Examiner*—Lorraine Spector
*Attorney, Agent, or Firm*—Hamilton, Brook, Smith & Reynolds, PC

[57] ABSTRACT

The present invention relates to the production and use of fusion proteins with an immunoglobulin hinge region linker.

20 Claims, No Drawings

OTHER PUBLICATIONS

Takeuchi, M., et al., "Role of Sugar Chains in the in Vitro Biological Activity of Human Erythropoietin Produced in Recombinant Chinese Hamster Ovary Cells," *J. Biol. Chem.*, 265(21):12127–12130 (1990).

Yonekura, S., et al., "Erythropoietin Receptors Induced By Dimethyl Sulfoxide Exhibit Positive Cooperativity Associated With an Amplified Biologic Response," *Proc. Natl. Acad. Sci. USA*, 88:2535–2539 (1991).

Grodberg, J., et al., "Functional and Structural Role of Arginine 103 in Human Erythropoietin," *Arch. Bioch. Bioph.*, 333(2):427–431 (1996).

Chern, Y., et al., "Structural Role of Amino Acids 99–110 in Recombinant Human Erythropoietin," *Eur. J. Biochem.*, 202:225–229 (1991).

Grodberg, J., et al., "Alanine Scanning Mutagenesis of Human Erythropoietin Identifies Four Amino Acids Which are Critical for Biological Activity," *Eur. J. Biochem.*, 218:597–601 (1993).

Jacobs, K., et al., "Isolation and Characterization of Genomic and cDNA Clones of Human Erythropoietin," Nature, 313:806–810 (1985).

Hollenbaugh, D., et al., "Cleavable CD40Ig Fusion Proteins and the Binding to sgp39," *J. Immuno. Meth.*, 188:1–7 (1995).

Sandlie, I. and Michaelsen, T.E., "Engineering the Hinge Region to Optimize Complement–induced Cytolysis," In *Antibody Engineering*, C.A.K. Borrebaeck, eds. (NY: W.H. Freeman and Company) pp. 69–88 (1992).

Hamers–Castermann, C., et al., "Naturally Occurring Antibodies Devoid of Light Chains," *Nature*, 363:446–448 (1993).

Terskjkh, A.V., et al., "Peptabody: A New Type of High Avidity Binding Protein," *Proc. Natl. Acad. Sci. USA*, 94:1663–1668 (1997).

McMahon, F.G., et al., "Pharmacokinetics and Effects of Recombinant Human Erythropoietin After Intravenous and Subcutaneous Injections in Healthy Volunteers," *Blood*, 76(9):1718–1722 (1990).

Spivak, J.L., et al., "The In Vivo Metabolism of Recombinant Human Erythropoietin in the Rat," *Blood*, 73(1):90–99, (Jan. 1989).

Knüli, C., et al., "Polyethylene Glycol (PEG) Modification of Granulocyte–Macrophage Colony Stimulating Factor (GM–CSF) Enhances Neutrophil Priming Activity but Not Colony Stimulating Activity," *British Journal Haematology*, 82:654–663 (1992).

Satake, R., et al., "Chemical Modification of Erythropoietin: An Increase in In Vitro Activity by Guanidination," *Biochimica et Biophysica Acta*, 1038:125–129 (1990).

Modi, N.B., "Pharmacokinetics and Pharmacodynamics of Recombinant Proteins and Peptides," *J. Controlled Release*, 29:269–281 (1994).

Batra, J.K., et al., "Insertion of Constant Region Domains of Human IgG into CD4–PE40 Increases its Plasma Half–Life," Mol. Immunology, 30(4):379–386 (1993).

Sytkowski, A.J., et al., "An Epo—Epo Fusion Protein with Enhanced Potency and Efficacy in vivo," Thirty–Ninth Annual Meeting of the American Society of Hematology, San Diego, California, USA, Dec. 5–9, 1997. *Blood 90* (Suppl. 1 Part 1). 1997. 57A. (Abstract 244).

Lunn, E.D., et al., "Erythropoietin Dimers with Enhanced in vivo Activity in Mice," Thirty–Eighth Annual Meeting of the American Society of Hematology, Orlando, Florida, USA, Dec. 6–10, 1996. *Blood 88* (10 Suppl. 1 Part 1–2). 1996. 543A. (Abstract 2161).

McGary, E.C., et al., "Post–transcriptional Regulation of Erythropoietin mRNA Stability by Erythropoietin mRNA–binding Protein," *The Journal of Biological Chemistry*, 272:8628–8634 (1997).

Sytkowski, A.J., "Human Erythropoietin Dimers with Markedly Enhanced in vivo Activity," *Proc. Natl. Acad. Sci. USA* 95:1184–1188 (1998).

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Glu Pro Lys Ser Cys Asp Lys Thr His Thr
1               5                   10

(2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Cys Pro Pro Cys Pro
1               5

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: single
        (D) TOPOLOGY: linear

```
        (ii) MOLECULE TYPE: peptide (xi) SEQUENCE DESCRIPTION: SEQ ID NO:3:

Ala Pro Glu Leu Leu Gly Gly Pro
1               5

(2) INFORMATION FOR SEQ ID NO:4:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Cys Cys Val Glu Cys Pro Pro Cys Pro
1               5

(2) INFORMATION FOR SEQ ID NO:5:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Ala Pro Pro Val Ala Gly Pro
1               5

(2) INFORMATION FOR SEQ ID NO:6:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Glu Leu Lys Thr Pro Leu Gly Asp Thr Thr His Thr
1               5                   10

(2) INFORMATION FOR SEQ ID NO:7:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Cys Pro Arg Cys Pro
1               5

(2) INFORMATION FOR SEQ ID NO:8:

(i) SEQUENCE CHARACTERISTICS:
            (A) LENGTH: 45 amino acids
            (B) TYPE: amino acid
            (C) STRANDEDNESS: single
            (D) TOPOLOGY: linear
```

(ii) MOLECULE TYPE: peptide (xi) SEQUENCE DESCRIPTION: SEQ ID NO:8:

Glu Pro Lys Ser Cys Asp Thr Pro Pro Cys Pro Arg Cys Pro Glu
1               5                   10                  15

Pro Lys Ser Cys Asp Thr Pro Pro Cys Pro Arg Cys Pro Glu Pro
                20                  25                  30

Lys Ser Cys Asp Thr Pro Pro Cys Pro Arg Cys Pro
        35                  40                  45

(2) INFORMATION FOR SEQ ID NO:9:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Ala Pro Glu Leu Leu Gly Gly Pro
1               5

(2) INFORMATION FOR SEQ ID NO:10:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Glu Pro Lys Ser
1

(2) INFORMATION FOR SEQ ID NO:11:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Cys Asp Thr Pro Pro Cys Pro Arg Cys Pro
1               5                   10

(2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Ala Pro Glu Leu Leu Gly Gly Pro
1               5

(2) INFORMATION FOR SEQ ID NO:13:

(i) SEQUENCE CHARACTERISTICS:
           (A) LENGTH: 7 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:13:

Glu Ser Lys Tyr Gly Pro Pro
1               5

(2) INFORMATION FOR SEQ ID NO:14:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:14:

Cys Pro Ser Cys Pro
1               5

(2) INFORMATION FOR SEQ ID NO:15:

(i) SEQUENCE CHARACTERISTICS:
           (A) LENGTH: 13 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:15:

Cys Pro Ser Cys Pro Ala Pro Glu Phe Leu Gly Gly Pro
1               5                  10

(2) INFORMATION FOR SEQ ID NO:16:

(i) SEQUENCE CHARACTERISTICS:
           (A) LENGTH: 6 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:16:

Val Pro Arg Asp Cys Gly
1               5

(2) INFORMATION FOR SEQ ID NO:17:

(i) SEQUENCE CHARACTERISTICS:
           (A) LENGTH: 7 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:17:

Cys Lys Pro Cys Ile Cys Thr
1               5

(2) INFORMATION FOR SEQ ID NO:18:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Val Pro Ser Glu Val Ser
1               5
```

(2) INFORMATION FOR SEQ ID NO:19:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Glu Pro Arg Gly Pro Thr Ile Lys Pro
1               5
```

(2) INFORMATION FOR SEQ ID NO:20:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Cys Pro Pro Cys Lys Cys Pro
1               5
```

(2) INFORMATION FOR SEQ ID NO:21:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Ala Pro Asn Leu Leu Gly Gly Pro
1               5
```

(2) INFORMATION FOR SEQ ID NO:22:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
GAGCCCAAAT CTTGTGACAA AACTCACACA TGCCCACCGT GCCCA          45
```

(2) INFORMATION FOR SEQ ID NO:23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

AGGCGCGGAG ATGGGGGTGC AC                                                  22

(2) INFORMATION FOR SEQ ID NO:24:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CAGTGTTCTA AACCCGAGAG ACAGGGGACA GGACGTCCGC C                       41

(2) INFORMATION FOR SEQ ID NO:25:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

ACCCGTACAC ACTCAAAACA GTGTTCTAAA CCCGAGAGAG A                       41

(2) INFORMATION FOR SEQ ID NO:26:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

ATCCTAGGCC CGTGCCACCC GTACACACTC AAAA                                34

(2) INFORMATION FOR SEQ ID NO:27:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

GCGGCAGTAC TGCCCCACCA CGCCTCATCT GTGACAGC                              38

(2) INFORMATION FOR SEQ ID NO:28:

(i) SEQUENCE CHARACTERISTICS:

```
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

CAGGTGGACA CACCTGGTCA TC                                                  22

(2) INFORMATION FOR SEQ ID NO:29:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

GAGCCCAGAG GGCCCACACT CAAGCCCTGT CCTCCATGCA AATGCCCA                      48

(2) INFORMATION FOR SEQ ID NO:30:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

ATAGGCCGCT AATCACTCCT CAGTGA                                              26

(2) INFORMATION FOR SEQ ID NO:31:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

ACACCCGGGA GACCCGAGGA CTCCCGAACA ACTCTACTA                                39

(2) INFORMATION FOR SEQ ID NO:32:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

ACCCTCCTGT CCCGAACTAA CACCCGGGAG ACCCGAGGAC                               40

(2) INFORMATION FOR SEQ ID NO:33:

(i) SEQUENCE CHARACTERISTICS:
        (A) LENGTH: 41 base pairs
        (B) TYPE: nucleic acid
        (C) STRANDEDNESS: single
        (D) TOPOLOGY: linear
```

-continued

```
    (ii) MOLECULE TYPE: DNA (genomic)

(xi) SEQUENCE DESCRIPTION: SEQ ID NO:33:

ATCCTAGACC CGTAAACGTA CCTCCTGTCC CGAACTAACA C                    41

(2) INFORMATION FOR SEQ ID NO:34:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:34:

ATGGATCCCT TCCACCTGCA GAAGG                                      25

(2) INFORMATION FOR SEQ ID NO:35:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:35:

GCAGATCTGA ATTTCGAATA TGTTCG                                     26
```

FUSION PROTEINS WITH AN IMMUNOGLOBULIN HINGE REGION LINKER

GOVERNMENT FUNDING

This invention was made, in whole or in part, with Government support under Department of the Navy Contract No. N000014-93-1-0776 and National Institutes of Health Grant No. R01 DK38841. The Government has certain rights in the invention.

BACKGROUND OF THE INVENTION

There is much interest in using biochemical or molecular biology techniques to produce therapeutic proteins with novel or enhanced properties. One desirable property is increasing biological activity, in particular increased circulating half-life of the protein.

Several methods have been employed to increase the biological activity of therapeutic proteins. These methods often focus on increasing the size of the therapeutic agents. One method of increasing a protein's size is through chemical cross-linking with another protein. For example, to increase the antigenicity of a protein, chemical cross-linking agents are used to conjugate the immunogenic protein to a carrier molecule such as immunoglobulin or serum albumin.

However, the conjugation of chemical compounds or inert molecules to a protein often results in a significant decrease of the overall biological activity of the protein, e.g., due to the conformational changes that occur, or due to increased steric hindrance as a result of the modification (Knusli, C., et al., *Brit. J. Haematol.*, 82:654–663 (1992)).

Alternatives, such as peptide linkers have also been used. For example, U.S. Pat. No. 5,073,627 describes the use of a peptide linker to join a Granulocyte-Macrophage Colony-Stimulating Factor (GM-CSF) protein molecule to an Interleukin-3 (IL-3) protein molecule to form a fusion protein. Conventional peptide linkers, however, can be rigid and inflexible. As a result, the linked protein often cannot "flex" into the desired biologically active conformation exhibited by the wild type protein, or the cross-linker or carrier protein sterically hinders biological activity. Thus, there is still a need for linkers suitable to link proteins in such a manner as to increase biological activity, such as increasing in vivo half life.

SUMMARY OF THE INVENTION

The present invention relates to fusion proteins with biological activity, and methods of making these fusion proteins through covalent linkage of two or more proteins, polypeptides, or biologically active fragments, variants, mutants, analogs or derivatives thereof. The fusion proteins of the present invention can also exhibit increased biological activity, as described herein. The covalent linkage is formed using immunoglobulin (Ig) hinge region amino acid sequences. The nucleic acids encoding the proteins of the fusion proteins are linked in tandem, meaning that the nucleic acids are linked, via nucleic acids encoding an Ig hinge region sequence, in succession. The term tandem is also an alternative means of describing the fusion proteins of this invention.

The proteins to be linked, or joined, are either identical, substantially similar, or different proteins. Importantly, the proteins can be attached to the hinge linker via either the carboxyl or amino terminus of the proteins. This is particularly advantageous in that such attachment allows the carboxyl terminus of the protein to be free to interact, or bind, to e.g., ligands or receptors.

In describing a fusion protein comprising only identical proteins or substantially similar proteins, the prefix "homo" is used. For example, the term homo-fusion protein describes a fusion protein comprising two or more identical, or substantially similar, protein molecules joined via the Ig hinge region amino acid sequence linker. In describing fusion proteins comprising more than one kind of protein, the prefix "hetero" is used. For example, hetero-fusion protein comprises two or more proteins joined together, with one or more of the proteins being different from one or more of the remaining proteins.

The fusion proteins of the present invention exhibit biological activity. The term "biological activity" as used herein, describes the activity of the endogenous, or wild type, non-fused protein. For example, a cytokine hinge-cytokine fusion protein has biological activity if the fusion protein exhibits the activity of non-fused cytokine (or cytokines, if different cytokines are fused).

Alternatively, the fusion proteins of the present invention can exhibit increased biological activity. Increased biological activity is defined, when used in reference to a fusion protein comprising identical or substantially similar proteins,, as a prolonged plasma half-life (i.e., a longer circulating half-life relative to the naturally occurring monomeric protein), or higher potency (i.e., requiring a smaller quantity relative to the naturally occurring protein to achieve a specified level of biological activity). Increased biological activity can also encompass a combination of the above-described activities, e.g., a fusion protein with higher potency that also exhibits a prolonged circulating half-life. Because the proteins of the present invention have increased biological activity, the frequency with which they must be administered is reduced, or the amount administered to achieve an effective dose is reduced. A reduced quantity of fusion protein would be necessary over the course of treatment than would be necessary if naturally occurring protein were used.

A fusion protein comprising different proteins is created for the purpose of exhibiting the increased biological activity described above and/or the novel characteristics of the different component proteins used in its construction. For example, a fusion protein consisting of erythropoietin (EPO) and human platelet-derived growth factor (PDGF) would be useful in cases of traumatic injury where the EPO component of the fusion protein would aid in the treatment of blood loss in a mammal, while the PDGF component would be useful in the repair of injured connective tissue. The hetero-fusion protein, containing two or more different proteins, can exhibit synergistic characteristics, and thus exhibit biological activity greater than the activity that would be exhibited by a similar quantity of each protein found in the fusion protein if each protein component were to be administered alone.

Any protein, polypeptide, or biologically active fragments, variants, mutants, analogs or derivatives thereof that can be linked to an immunoglobulin hinge region and that has therapeutic activity can be used in the present invention. Specifically encompassed by this invention are cytokines, growth factors, and hormones which include, for example, the following: Interferon-α, Interferon-β, Interferon-γ, Interleukin-1, Interleukin-2, Interleukin-3, Interleukin-4, Interleukin-5, Interleukin-6, Interleukin-7, Interleukin-8, Interleukin-9, Interleukin-10, Interleukin-11, Interleukin-12, Interleukin-13, Interleukin-14, Interleukin- 15, Interleukin-16, Erythropoietin, Colony-Stimulating Factor-1, Granulocyte Colony-Stimulating Factor, Granulocyte-Macrophage Colony-Stimulating Factor, Leukemia Inhibitory Factor, Tumor Necrosis Factor, Lymphotoxin, Platelet-Derived Growth Factor, Fibroblast Growth Factors, Vascular Endothelial Cell Growth Factor, Epidermal Growth Factor, Transforming Growth Factor-β, Transforming Growth Factor-α, Thrombopoietin, Stem Cell Factor, Oncostatin M, Amphiregulin, Mullerian-Inhibiting Substance, B-Cell Growth Factor, Macrophage Migration Inhibiting Factor, Endostatin, and Angiostatin.

More specifically, the present invention relates to a homo-fusion protein wherein two erythropoietin (EPO) molecules are linked by an amino acid sequence comprising an immunoglobulin hinge region sequence and wherein the homo-fusion protein has increased biological activity, as defined above. The present invention also relates to a hetero-fusion protein wherein IL2 is linked via a hinge region sequence to FasL, and wherein the IL2-FasL fusion protein has biological activity.

The present invention also relates to methods of producing a fusion protein comprising an immunoglobulin hinge region which is used to join two or more protein molecules that are identical, substantially similar, or different, as defined above.

The present invention also relates to methods of using the fusion proteins described herein. The fusion proteins of the present invention can be used in the same manner as the non-fused, wild type protein, especially where an increased biological activity is desirable. For example, EPO fusion proteins of the present invention, which have a longer in vivo half-life than non-fused wild type EPO, can be used to treat various anemic conditions, as described further below.

As a result of the work described herein, homo- and hetero-fusion proteins with increased biological activity are now available. These fusion proteins can be injected less frequently, or at the same frequency but in smaller doses, relative to the wild type protein, possibly with fewer side-effects.

DETAILED DESCRIPTION OF THE INVENTION

The present invention relates to biologically active fusion proteins comprising one or more proteins linked by an amino acid sequence comprising the hinge region sequence of an immunoglobulin.

The basic immunoglobulin, or Ig, structural unit is known to comprise a tetramer, each tetramer having two identical pairs of polypeptide chains. These polypeptide chains are designated as "light" (L) and "heavy" (H) in reference to their molecular weight. The N-terminal portion of each chain defines a variable (V) region primarily responsible for antigen recognition. The C-terminal portion of each chain defines a constant (C) region primarily responsible for effector function.

Within the light and heavy chains, units made up of about 110 amino acids form discrete domains. Each domain is held together by a single, internal disulfide bond. The heavy chain typically contains 4 such domains, while the light chain typically contains 2 domains. The COOH terminus of the first N-terminal domain of the heavy chain, $V_H$, interacts with the N-terminal domain of the light chain, $V_L$, to produce the binding region of the antibody. Moving towards the C-terminus, the next three domains of the heavy chain are designated $C_H1$, $C_H2$, and $C_H3$, respectively.

Most heavy chains have a hinge region between the $C_H1$ and $C_H2$ domains consisting of a small number of amino acids. The hinge is flexible and allows the binding region to move freely relative to the rest of the molecule. At the hinge region are the disulfide bridges which hold the two dimers together, creating the tetramer structural unit.

There are five classes of immunoglobulins (IgA, IgD, IgE, IgG, and IgM) in higher vertebrates, all of which contain a hinge region. Additionally, some of these classes of immunoglobulins have subclasses, e.g., IgG has four subclasses ($IgG_1$, $IgG_2$, $IgG_3$, and $IgG_4$). (Alberts, B. et al., Chapter 23: The Immune System, In Molecular Biology of the Cell, 3d Edition, Garland Publishing, Inc., New York, N.Y.). The amino acid sequences of hinge regions from these classes of immunoglobulins and subclasses, as well as classes and subclasses from other species, are encompassed by this invention.

The hinge region is often divided into three regions: the upper, middle, and lower hinge. The upper hinge is defined as the number of amino acids between the end of the first domain of the heavy chain ($C_H1$) and the first cysteine forming an interheavy chain disulfide bridge. The middle hinge is high in proline and contains the inter-heavy chain cysteine disulfide bridges. The lower hinge connects the middle hinge to the $C_H2$ domain. See Sandlie, I. and Michaelsen, T., Chapter 3: Engineering the Hinge Region to Optimize Complement-induced Cytolysis, In Antibody Engineering: A Practical Guide, W. H. Freeman and Co., New York, N.Y., the teachings of which are herein incorporated by reference in their entirety. See also Hamers-Casterman, C., Naturally Occurring Antibodies Devoid of Light Chains, 363 Nature 446 (1993) and Terskikh, A. V., "Peptabody": A New Type of High Avidity Binding Protein, 94 Proc. Natl. Acad. Sci. USA 1663 (1997), the teachings of both of which are herein incorporated by reference in their entirety.

Previous research has identified the amino acid sequences of these three hinge regions in some human and mouse subclasses indicated in the Table.

TABLE

HUMAN AND MOUSE IMMUNOGLOBULIN HINGE SEQUENCES

| | Upper Hinge | Middle Hinge | Lower Hinge |
| --- | --- | --- | --- |
| Human IgG$_1$ | EPKSCDKTHT (SEQ ID NO: 1) | CPPCP (SEQ ID NO: 2) | APELLGGP (SEQ ID NO: 3) |
| Human IgG$_2$ | ERK | CCVECPPCP (SEQ ID NO: 4) | APPVAGP (SEQ ID NO: 5) |
| Human IgG$_3$ | ELKTPLGDTTHT (SEQ ID NO: 6) | CPRCP (SEQ ID NO: 7) (EPKSCDTPPPCPRCP)$_3$ (SEQ ID NO: 8) | APELLGGP (SEQ ID NO: 9) |

TABLE-continued

HUMAN AND MOUSE IMMUNOGLOBULIN HINGE SEQUENCES

|  | Upper Hinge | Middle Hinge | Lower Hinge |
| --- | --- | --- | --- |
| Human IgG$_3$M15 | EPKS<br>(SEQ ID NO: 10) | CDTPPPCPRCP<br>(SEQ ID NO: 11) | APELLGGP<br>(SEQ ID NO: 12) |
| Human IgG$_4$ | ESKYGPP<br>(SEQ ID NO: 13) | CPSCP<br>(SEQ ID NO: 14) | APEFLGGP<br>(SEQ ID NO: 15) |
| Mouse IgG$_1$ | VPRDCG<br>(SEQ ID NO: 16) | CKPCICT<br>(SEQ ID NO: 17) | VPSEVS<br>(SEQ ID NO: 18) |
| Mouse IgG$_{2A}$ | EPRGPTIKP<br>(SEQ ID NO: 19) | CPPCKCP<br>(SEQ ID NO: 20) | APNLLGGP<br>(SEQ ID NO: 21) |

As used herein, the term Ig "hinge" region refers to a polypeptide comprising an amino acid sequence that shares sequence identity, or similarity, with a portion of a naturally-occurring Ig hinge region sequence, which includes the cysteine residues at which the disulfide bonds link the two heavy chains of the immunoglobulin. Sequence similarity of the hinge region linkers of the present invention with naturally-occurring immunoglobulin hinge region amino acid sequences can range from at least 50% to about 75–80%, and typically greater than about 90%.

Derivatives and analogs of the hinge region can be obtained by mutations. A derivative or analog, as referred to herein, is a polypeptide comprising an amino acid sequence that shares sequence identity, or similarity, with the full-length sequence of the wild type (or naturally occurring protein), except that it has one or more amino acid sequence differences attributable to a deletion, insertion and/or substitution.

The present invention also encompasses fragments of the hinge region. Such a fragment need only be long enough to allow the proteins attached by the hinge region fragment to attain a biologically active conformation.

The fusion proteins of the present invention typically are joined by the fusion of the C-terminal of one protein to the N-terminal of the Ig hinge region and the fusion of the N-terminal of a second protein to the C-terminal of the protein-hinge complex. Thus, the fusion proteins of the present invention have a formula of $R_1$-L-$R_2$, where $R_1$ is a protein, $R_2$ is an identical or substantially similar protein to $R_1$, and L (Linker) is an Ig hinge region sequence. Alternatively, the fusion proteins of the present invention have a formula of $R_1$-L-$R_2$, where $R_1$ is a protein, $R_2$ is a different, or substantially different, protein from $R_1$, and L (Linker) is an Ig hinge region. The proteins are linked to one another in such a manner so as to produce a single protein which retains the biological activity of each of the proteins in the fusion protein.

However, the level of biological activity of the naturally-occurring protein, or fragments, analogs, mutants, variants or derivatives thereof, need not be identical to the activity of the naturally-occurring protein (also referred to herein as the parent protein). For example, a fragment of a cytokine protein may exhibit only 50–80% of the activity of the naturally-occurring cytokine, yet because two or more cytokines are linked to form a fusion protein, the fusion protein will still exhibit increased biological activity as compared to a single molecule of the naturally-occurring cytokine. Tests to determine biological activity that are specific for each protein component are well-known to those of skill in the art and can include, for example, measuring increased hematopoiesis, platelet production or receptor binding. For example, the biological activity of a mutant of erythropoietin can be measured as described in U.S. Pat. Nos. 5,614,184 and 5,580,853, the teachings of which are herein incorporated by reference in their entirety.

Fusion protein constructs are named by listing the respective molecules. For example, EPO-L-EPO refers to a homo-fusion protein comprised of two EPO molecules joined by an Ig hinge region. Similarly, EPO-L-EPO-L-EPO can refer to a homo-fusion protein comprised of three EPO molecules with an Ig hinge region between each of the three EPO molecules. Other combinations, such as hetero-fusion proteins are possible, e.g., EPO-L-EPO-L-IL3 and EPO-L-IL3-L-IL3. Where there is more than one Ig hinge region, a single Ig hinge region can be attached to another Ig hinge region in the fusion protein, e.g., EPO-L-L-EPO.

It is important to note that the protein, e.g., erythropoietin, can be attached (e.g., joined or linked) to the hinge via either its amino-or carboxyl-terminus. For example, as described herein, a fusion protein has been produced, IL2-hinge-FasL, where the proteins are attached to the hinge via the amino terminus. Alternatively, the attachment is made to the hinge via the carboxyl-terminus of the protein.

PRODUCTION OF FUSION PROTEINS

The term "recombinant," as used herein, means that a protein is derived from recombinant (e.g., microbial, viral, insect or mammalian) expression systems. "Microbial" refers to recombinant proteins made in bacterial or fungal, e.g. yeast, expression systems. Proteins expressed in most bacterial cultures will be free of glycan. Proteins expressed in yeast may have a glycosylation pattern different from that of proteins expressed in mammalian cells.

As used herein, the term "nucleotide sequence" or "nucleic acid sequence" refers to a heteropolymer of deoxyribonucleotides (DNA) or ribonucleotides (RNA). Nucleic acid sequences encoding the proteins provided in this invention can be assembled from DNA, either cDNA or genomic DNA, or RNA and short oligonucleotide linkers to provide a synthetic nucleic acid sequence which is capable of being expressed in a recombinant transcriptional unit.

The term "recombinant expression vector," as used herein, refers to a replicable DNA construct used either to amplify or to express DNA which encodes the fusion proteins of the present invention and which includes a transcriptional unit comprising an assembly of (1) a genetic element or elements having a regulatory role in gene expression, for example, promoters or enhancers; (2) a structural or coding sequence which is transcribed into mRNA and translated into protein; and (3) appropriate transcription and translation initiation and termination sequences. Structural elements intended for use in yeast expression systems preferably include a leader sequence enabling extracellular secretion of translated protein by a host cell. Alternatively, where recombinant protein is expressed without a leader sequence or transport sequence, it may include an N-terminal methionine residue. This residue may optionally be subsequently cleaved from the expressed recombinant protein to provide a final product.

A DNA sequence encoding a fusion protein can be produced using recombinant DNA techniques to assemble separate DNA sequences encoding a protein and Ig hinge region. This DNA construct encoding the protein-linker-protein sequence is then inserted into an appropriate expression vector. For example, the 3' end of a DNA sequence encoding a protein is ligated to the 5' end of a DNA sequence encoding an Ig hinge region. The 3' end of this protein-hinge DNA sequence is then ligated to the 5' end of a second DNA sequence encoding the same or a different protein, with the reading frames of the sequences in phase to permit mRNA translation of the sequences into a single biologically active fusion protein. The regulatory elements responsible for transcription of DNA into mRNA are retained on the protein-hinge complex DNA sequence while binding signals or stop codons, which would prevent read-through to the second protein DNA sequence, are eliminated. Conversely, regulatory elements are removed from the second protein DNA sequence while stop codons required to end translation are retained.

Nucleic acids encoding the fusion proteins of the present invention can also be produced synthetically using purine and pyrimidine bases and nucleic acid synthesis techniques well-known in the art.

The present invention provides fusion proteins comprising two or more molecules of protein. The fusion proteins of the present invention also include various structural forms of the primary protein which retain biological activity. Individual amino acid residues, for example, may be modified by oxidation or reduction. See, for example, U.S. Pat. No. 5,614,184 the teachings of which are hereby incorporated by reference, in their entirety.

The present invention specifically encompasses biologically active fragments, analogs, mutants, variants and derivatives of the proteins described herein. An "analog" is defined herein to mean an amino acid sequence with sufficient amino acid sequence similarity to the amino acid sequence of endogenous protein to possess the biological activity of the endogenous protein. For example, an analog of a polypeptide can be encoded by a nucleic acid sequence which has "silent" changes in the sequence resulting in a polypeptide wherein one or more amino acid residues differ from the amino acid sequence of the protein, yet possess qualities of the protein. Examples of such differences include additions, deletions or substitutions of residues.

The present invention also encompasses biologically active fragments of a protein. Such fragments can include only a part of the full-length amino acid sequence of the protein yet possess biological activity. As used herein, a "biologically active fragment" means a fragment that can exert a biological or physical effect of the full-length protein, or has a biological characteristic of the full-length protein. Such fragments can be produced by amino and carboxyl terminal deletions as well as internal deletions. Also included are active fragments of the protein as obtained by enzymatic digestion.

Biological activity can be tested using methods well-known to those of skill in the art. For example, the fusion proteins of the present invention have biological or therapeutic activity for use in mammals (e.g., veterinary use) and specifically in humans. If the fusion protein is a hetero-fusion protein, the activity of each of the two or more proteins comprising the hetero-fusion protein can be tested. For example, a GM-CSF/IL-3 fusion protein can be used to treat leukemias in dogs. The GM-CSF activity can be tested for the ability to stimulate proliferation of AML-193 cells in a thymidine incorporation assay, as described in U.S. Pat. No. 5,073,627, which is herein incorporated by reference in its entirety. IL-3 activity can be tested by techniques well-known to those of skill in the art.

For example, erythropoietin fusion proteins can be tested for biological activity using the method of Krystal (Krystal, G., *Exp. Hematol.*, 11:649–660 (1983)), the teachings of which are herein incorporated by reference in their entirety. Briefly, the bioassay of Krystal measures the effect of erythropoietin on intact mouse spleen cells. Mice are treated with phenylhydrazine to stimulate production of red blood cell precursor cells in the spleen. After treatment, the spleens are removed, intact spleen cells are carefully isolated and incubated with various amounts of wild type erythropoietin or an erythropoietin fusion protein as described herein. After an overnight incubation, H thymidine is added and its incorporation into cellular DNA is measured. The amount of H thymidine incorporation is indicative of erythropoietin-stimulated production of red blood cells via interaction of erythropoietin with its cellular receptor.

"Derivatives" and "variants" of a protein are proteins that have been modified. They include proteins that have been modified by alterations in their amino acid sequence. They also include truncated and hybrid forms of the protein. "Truncated" forms are shorter versions of a protein, typically modified so as to remove the C-terminal regions which effect binding or secretion. "Hybrid" or "chimeric" forms are proteins that are composed of one or more proteins combined with one or more other proteins.

The present invention also provides proteins with or without associated native-protein glycosylation. Expression of DNAs encoding the fusion proteins in bacteria such as *E. coli* provides non-glycosylated molecules. Functional mutant analogs having inactivated N-glycosylation sites can be produced by oligonucleotide synthesis and ligation or by site-specific mutagenesis techniques. These analog proteins can be produced in a homogeneous, reduced carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine (Asn) provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$.

Derivatives and analogs may also be obtained by mutations of the fusion protein. Analogs of fusion proteins may be constructed by, for example, making various substitutions of residues or sequences. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present. Generally, substitutions should be made conservatively. The most preferred substitute amino acids are those having physicochemical characteristics resembling those of the residue to be replaced. Similarly, when a deletion or insertion strategy is adopted, the potential effect of the deletion or insertion on biological activity should be considered.

Mutations in nucleotide sequences constructed for expression of analogs must, of course, preserve the reading frame phase of the coding sequences and preferably will not create complementary regions that could hybridize to produce secondary mRNA structures such as loops or hairpins which would adversely affect translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for the desired activity.

Mutations can be introduced at particular loci by synthesizing oligonucleotides encoding the desired amino acid residues, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, Jan. 12–19, 1985); Smith et al. (*Genetic Engineering: Principles and Methods*, Plenum Press, 1981); and U.S. Pat. Nos. 4,518,584 and 4,737,462, which are incorporated herein by reference.

The present invention also provides recombinant expression vectors which include synthetic or cDNA-derived DNA sequences encoding fusion proteins comprising the fusion protein operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. The ability to replicate in a host, usually conferred by an origin of replication, and a selection sequences to facilitate recognition of transformants may additionally be incorporated. Generally, operably linked means contiguous.

Host cells are cells which have been transfected with fusion protein vectors constructed using recombinant DNA techniques. Transformed host cells ordinarily express the desired fusion protein, but host cells transformed for purposes of cloning or amplifying DNA do not need to express the protein. Expressed fusion protein will generally be secreted into the culture supernatant. Suitable host cells for expression of fusion protein include prokaryotes, yeast or higher eukaryotic cells in which the gene is under the control of appropriate promoters. Prokaryotes include gram negative or gram positive organisms, for example *E. coli*. Higher eukaryotic cells include established cell lines of mammalian origin as described below. Cell-free translation systems could also be employed to produce fusion protein using RNAs derived from the DNA constructs of the present invention. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), which is incorporated herein by reference.

Prokaryotic expression vectors generally comprise one or more phenotypic selection markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomonas, Streptomyces, and Staphyolococcus, although others may also be employed as a matter of choice.

Expression vectors suitable for use in bacteria can comprise a selectable marker and bacterial origin of replication derived from commercially available plasmids comprising genetic elements of the well-known cloning vector pBR322 (ATCC 37017). Such commercial vectors include, for example, pKK223-3 (Pharmacia Fine Chemicals, Uppsala, Sweden) and pGEM1 (Promega Biotech, Madison, Wis.). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the blactamase (penicillinase)and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980) and tac promoter (Maniatis, *Molecular Cloning: A Laboratory Manual*, Cold Spring Harbor Laboratory, 1982).

Recombinant fusion proteins may also be expressed in yeast hosts, preferably from the Saccharomyces species, such as *S. cerevisiae*. Yeast of other genera such as Pichia or Kluyveromyces may also be employed. Yeast vectors will generally contain an origin of replication from a yeast plasmid or an autonomously replicating sequence (ARS), promoter, DNA encoding the fusion protein, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trpl lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triose-phosphate isomerase, phosphoglucose isomerase, and glucokinase. Suitable vectors and promoters for use in yeast expression are well-known within the art.

Preferred yeast vectors can be assembled using DNA sequences from pBR322 for selection and replication in *E. coli* (Amp gene and origin of replication) and yeast DNA sequences including a glucose-repressible ADH2 promoter and α-factor leader, which directs secretion of heterologous proteins, can be inserted between the promoter and the structural gene to be expressed (Kurjan et al., *Cell* 30:933, 1982; and Bitter et al., *Proc. Natl. Acad. Sci. USA* 81:5330, 1984). The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen et al., *Proc. Natl. Acad. Sci. USA* 75:1929, 1978, selecting for Trp$^+$transformants in a selective medium consisting of 0.67% yeast nitrogen base, 0.5% casamino acids, 2% glucose, 10 µg/ml adenine and 20 µg/ml uracil.

Host strains transformed by vectors comprising the ADH2 promoter may be grown for expression in a rich medium consisting of 1% yeast extract, 2% peptone, and 1% glucose supplemented with 80 µg/ml adenine and 80 µg/ml uracil. Derepression of the ADH2 promoter occurs upon exhaustion of medium glucose. Crude yeast supernatants are harvested by filtration and held at 4° C. prior to further purification. Various mammalian or insect cell culture systems can be employed to express recombinant protein. Baculovirus systems for production of heterologous proteins in insect cells are reviewed by Luckow and Summers, *Bio/Technology* 6:47 (1988). Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese Hamster Ovary (CHO), HeLa and BHK cell lines. Mammalian expression vectors may comprise non-transcribed elements such as an origin of replication, a suitable promoter and enhancer linked to the gene to be expressed, and other 5' or 3' flanking nontranscribed sequences, and 5' to 3' nontranslated sequences, such as necessary ribosome binding sites, a poly-adenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin or replication (Fiers et al., *Nature* 273:113, 1978). Smaller or larger SV40 fragments may also be used, provided the approximately 250 bp sequence extending from the Hind III site toward the BglI site located in the viral origin of replication is included. Exemplary vectors can be constructed as disclosed by Okayama and Berg (*Mol. Cell. Biol.* 3:280, 1983).

Preferred eukaryotic vectors for expression of EPO DNA include pIXY321 and pIXY344, both of which are yeast expression vectors derived from pBC102. K22(ATCC 67,255) and contain DNA sequences from pBR322 for selection and replication in *E. coli* (Apr gene and origin of replication) and yeast.

Purified mammalian fusion proteins or analogs are prepared by culturing suitable host/vector systems to express the recombinant translation products of the DNAs of the present invention, which are then purified from culture media or cell extracts. For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix.

Finally, one or more reverse phase high performance liquid chromatography (RP-HPLC) media, e.g., silica gel having pendant methyl or other aliphatic groups, can be employed to further purify a fusion protein composition. Some or all of the foregoing purification steps, in various combinations, can also be employed to provide a homogenous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant fusion proteins can be disrupted by any convenient method, including freeze-thaw cycling, sonication, mechanical disruption, or use of cell lysing agents.

Fermentation of yeast which express fusion proteins as a secreted protein greatly simplifies purification. Secreted recombinant protein resulting from a large scale fermentation can be purified by methods analogous to those disclosed by Urdal et al. (*J. Chromatog.* 296:171, 1984).

Fusion protein synthesized in recombinant culture is characterized by the presence of non-human cell components, including proteins, in amount and of a character which depend upon the purification steps taken to recover the fusion protein from the culture. These components ordinarily will be of yeast, prokaryotic or non-human higher eukaryotic origin and preferably are present in innocuous contaminant quantities, on the order of less than about 5 percent by scanning densitometry or chromatography. Further, recombinant cell culture enables the production of the fusion protein free of proteins which may be normally associated with the naturally-ocurring protein as they are found in nature in their respective species of origin, e.g., in cells, cell exudates or body fluids.

USES OF FUSION PROTEINS

The fusion proteins of the present invention can be used for the prevention or treatment of many conditions or deficiencies in mammalian species by physicians and/or veterinarians. The amount of biologically active fusion protein used in the treatment of various conditions will, of course, depend upon the severity of the condition being treated, the route of administration chosen, and the specific activity or purity of the fusion protein, and will be determined by the attending physician or veterinarian. Pharmaceutical compositions suitable for administration comprise the fusion protein in an effective amount and a physiologically acceptable carrier. An effective amount, as used herein, is defined as that quantity which alleviates, to any degree, or eliminates the condition for which the mammal is being treated.

The erythropoietin fusion proteins of the present invention can be used, for example, in the treatment of anemia associated with renal failure, chronic disease, blood loss or cancer in mammals.

Compositions of the present invention can be administered by a variety of routes, including, but not limited to, parenteral (e.g., injection, including but not limited to, intravenous, intraarterial, intramuscular, subcutaneous; inhalation, including but not limited to, intrabronchial, intranasal or oral inhalation, intranasal drops; topical) and non-parenteral (e.g., oral, including but not limited to, dietary; rectal).

The carriers will be non-toxic to recipients at the dosages and concentrations employed. The formulation used will vary according to the route of administration selected (e.g., solution, emulsion, capsule). For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers. See, generally, *Remington's Pharmaceutical Science*, 16th Edition, Mack, Ed. (1980). For inhalation, the compound can be solubilized and loaded into a suitable dispenser for administration (e.g., an atomizer, nebulizer or pressurized aerosol dispenser). Fusion proteins can be administered individually, together or in combination with other drugs or agents (e.g., other chemotherapeutic agents, immune system enhancers).

Fusion protein compositions may be used to enhance proliferation, differentiation and functional activation of hematopoietic progenitor cells, such as bone marrow cells. Specifically, compositions containing the fusion protein may be used to increase peripheral blood leukocyte numbers and increase circulating granulocyte counts in myelosuppressed patients. To achieve this result, a therapeutically effective quantity of a fusion protein composition is administered to a mammal, preferably a human, in association with a pharmaceutical carrier or diluent.

The present invention is further illustrated by the following examples, which are not intended to be limiting in any way.

EXAMPLE 1

PRODUCTION OF AN ERYTHROPOIETIN HOMO-FUSION PROTEIN

One molecule having great therapeutic value, but with a number of problems that might benefit through attachment to the hinge region of an immunoglobulin molecule, is erythropoietin (EPO). Erythropoietin is typically administered by intravenous or subcutaneous injection three times weekly at a dose of approximately 25–100 U/kg, at a yearly cost of several thousand dollars. Moreover, when using injectable pharmaceuticals, the frequency at which those injections must be made in order to maintain a therapeutic level of the compound in the circulation is a problem.

CONSTRUCTION OF THE EPO-EPO DIMER

The nucleotide sequence of wild type erythropoietin can be obtained from Jacobs, K., et al., *Nature* 323:806(1985), which is herein incorporated by reference in its entirety.

An EPO-EPO fusion protein is constructed by linking two strands of EPO cDNA with a DNA strand encoding the immunoglobulin hinge polypeptide: GAGCCCAAATCT-TGTGACAAAACTCACACATGCCCACCAC-CGTGCCCA (SEQ ID NO: 22). The initial preceding EPO DNA strand, referred to herein as EPO A is generated by the Polymerase Chain Reaction (PCR) using EPO specific synthetic oligonucleotides. The linking DNA strand is sequentially lengthened to the proposed length by using psv2-EPO as template and 3' primers with appropriately extended 3' ends encoding the hinge region of human IgG1. The 5' oligonucleotide inserts a unique Not I restriction site 10 nucleotides 5' to the translational start codon, while the 3' oligonucleotide eliminates the termination codon and extend 18 nucleic acid sequence encoding the first 6 amino acid of hinge. By using two sequential PCR with synthetic 3' oligonucleotides, 27 nucleic acid sequences encoding last 9 amino acid of hinge region is extended 3' to EPO A sequence and a unique BamHI restriction site is inserted 3' to the hinge. Synthetic oligonucleotides used for the amplification of the EPO DNA strand after the linker (EPO B DNA) change the first codon from Ala to Asp, creating a unique BamHI site spanning the 5' end of the EPO DNA encoding the mature protein and introducing a unique XbaI site 3' to the termination code.

EPO A and EPO B DNA are produced by using the Polymerase Chain Reaction (PCR) and a human EPO cDNA plasmid, psv2-EPO (Chern Y. J., et al., *Eur J Biochem* 202:225(1991)) as template. Primers used to produce EPO A are as follows: 5'-AGGCGCGGAGATGGGGGTGCAC (SEQ ID NO: 23), 3'-CAGTGTTCTAAA CCCGAGAGA-CAGGGGACAGGACGTCCGCC (SEQ ID NO: 24), 3'-ACCCGTACACACTCAAAACAGTGTTCTAAACCC-GAGAGAGA (SEQ ID NO: 25), and 3'-ATCCTAGGCCCGTGCCACCCGTACACACTCAAAA (SEQ ID NO: 26). Primers used to produce EPO B are as follows: 5'-GCGGCAGTACTGCCCCACCACGCCT-CATCTGTGACAGC (SEQ ID NO: 27) and 3'-CAGGTGGACACACCTGGTCATC (SEQ ID NO: 28).

PCR reactions (50 µl) contain the following components: 0.5 µM of 5' primer or 3' primer; 10 ng psv2-EPO; 200 µM of dATP, dCTP, dGTP, or dTTP; 20 mM Tris-HCl (pH 8.0); 2 mM $MgCl_2$; 10 mM KCl; 6 mM $(NH_4)_2SO_4$; 0.1% Triton X-100; 10 µg/ml nuclease-free BSA; and 2.5 U Pfu DNA Polymerase (Stratagene). The reactions are overlaid with mineral oil (50 µl; Molecular Biology Grade, Sigma) and subjected to 25 cycles of 94° C. for 1 min (denaturation), of 52° C. for 1 min (annealing) and of 72° C. for 1 min (extension) in a Perkin Elmer DNA Thermal Cycler 480.

Next, the DNA sequences of the PCR products are determined. First, the PCR products are purified from a 1% agarose gel using the QIAQUICK™ Gel Extraction Kit. They are ligated to pCR-blunt, in which the reactions contain an insert to vector molar ratio of 10 to 1. The ligation reactions (10 µl) contain the gel-purified PCR products, 25 ng of PCR-blunt, 1× ligation buffer and 4 U of T4 DNA ligase (ZERO BLUNT™ PCR Cloning Kit, Invitrogen). Incubations are carried out for 1 hour at 16° C.

TOP 10™ Competent Cells (Invitrogen) are transformed according to procedure established by Invitrogen: 2 µl of β-mercaptoethanol is added to the cells on ice, mixed by gentle swirling with a pipette tip, followed by 2 µl of the ligation described in the preceding paragraph. This mixture is incubated on ice for 30 min, followed by exactly 45 seconds at 42° C. The vial is then placed on ice for 2 min. 250 µl of pre-warmed (37° C.) SOC medium containing 2% tryptone, 0.5% yeast extract, 10 mM NaCl, 2.5 mM KCl, 10 mM $MgCl_2$, 10 mM $MgSO_4$, and 20 mM glucose is then added and the cells shaken for 1 hr at 37° C. 50 µl of a 1:5 dilution of transformed cells are plated on LB (Miller's modification, Sigma) agar plates containing 50 µg/ml kanamycin and X-gal. The plates are incubated at 37°(overnight. Colonies are plucked and 2.5 ml LB containing 50 µg/ml kanamycin are inoculated with these colonies. Plasmid DNA are prepared from the overnight cultures using Promega's WIZARD PLUS MINIPREPS™ DNA Purification System. Clones are analyzed by restriction digest fragment analysis.

The pCRBlunt-EPO A and pCRBlunt-EPO B DNA clones are digested with BglI, which would give unique-sized fragments for a correctly inserted DNA and an insert oriented in the reverse direction. Clones with inserts in the reverse direction are chosen and larger amounts (from 100 ml of LB/50 µg/ml kanamycin) of DNA plasmids prepared using Promega's WIZARD PLUS MAXIPREPS™ DNA Purification System. Clones with inserts in the 'forward' direction produce the proposed EPO-EPO DNA.

The EPO A DNA strand is linked to the EPO B DNA strand using the procedure described as follows. pCRBlunt-EPO A(−) are digested with BamHI and Not I and the 677 bp fragment gel purified. pCRBlunt-EPO B(−) is digested with BamHI and XbaI and the 557 bp fragment gel purified. The EPO A 677 bp fragment is then ligated to the EPO B 557 bp fragment in a 1:1 molar ratio of EPO A 677 bp fragment to EPO B 557 bp fragment. Ligations are carried out overnight at 16° C. The ligated EPO A-EPO B DNA fragments are purified using QIAQUICK™ Gel Extraction Kit and ligated to pcDNA2.1(−) which have previously been digested with NotI and XbaI and gel purified. The ligation reaction contains a 5:1 molar ratio of DNA insert to pcDNA2.1(−). The incubation is carried out overnight at 16° C. Clones are picked from ampicillin-resistant colonies by restriction digest analysis, produced in microgram quantities, and used to transfect COS I cells.

TRANSIENT EXPRESSION OF EPO DIMER IN COS I CELLS

COS I cells are grown to 70% confluency in Dulbecco's Modified Eagle Medium, high glucose (4.5 g/L; Gibco), 10% fetal bovine serum (Hyclone) in the presence of 100 U penicillin, 100 µg streptomycin, 250 ng Fungizone per ml of tissue culture medium (antibiotic-antimycotic cocktail from Gibco) at 37° C. and 10% $CO_2$. The cells are harvested by trypsinizing using 0.05% Trypsin, 0.53 mM EDTA (Gibco) and washing twice with phosphate buffered saline (PBS)/6 mM glucose solution. Cells are suspended in the above PBS/glucose buffer to a concentration of $2 \times 10^6$ cells/ml. 0.5 ml of cells are placed in electroporation cuvettes (0.4 cm gap, Bio-Rad) and 10 µg of pcDNA/EPO-EPO added. The cells are electroporated under the following conditions: voltage=0.3 kV, field strength=0.75 kV/cm, capacitor=250 µF, and resistor =none (Pulse controller set at Ω). Cells are plated in 30 ml of pre-warmed DMEM, high glucose, 10% FBS and incubated for 72 h at 37° C. and 10% $CO_2$. The controls are 10 µg of pcDNA-EPO and 10 µg of pcDNA 2.1(−).

The conditioned media is collected and centrifuged at 13,800×g for 10 min at 4° C. 1 ml aliquots of each conditioned media are dialyzed against Minimum Essential Medium α overnight with 3× changes of medium. These samples are assayed for EPO activity by the method of Krystal.

STABLE EXPRESSION OF EPO DIMER IN CHO CELLS

Chinese Hamster Ovary cells (CHO) and NS.1 myeloma cells can be used for stable expression of EPO-EPO protein.

CHO cells are grown to 70% confluency in Dulbecco's Modified Eagle Medium, high glucose (4.5 g/L; Gibco), 10% fetal bovine serum (Hyclone) in the presence of 100 U penicillin, 100 µg streptomycin, 250 ng Fungizone per ml of tissue culture medium (antibiotic-antimycotic cocktail from Gibco) at 37° C. and 10% $CO_2$. The cells are harvested by trypsinizing using 0.05% Trypsin, 0.53 mM EDTA (Gibco) and washing twice with phosphate buffered saline (PBS)/6 mM glucose solution. Cells are suspended in the above PBS/glucose buffer to a concentration of $2 \times 10^6$ cells/ml. 0.5 ml of cells are placed in electroporation cuvettes (0.4 cm gap, Bio-Rad) and 20 µg of linearized pcDNA/EPO-EPO plasmid DNA is added. The cells are electroporated under the following conditions: voltage=1.5 kV, field strength= 0.75 kV/cm, capacitor=3 µF, and resistor=none (Pulse controller set at Ω). Cells are plated in 30 ml. of pre-warmed DMEM, high glucose, 10% FBS containing 1.5 mg/ml of G418 (geneticin, Gibco BRL) and incubated at 37° C. and 5% $CO_2$. After subcloning, high producing clones are selected by screening supernatants for EPO by ELISA (PharMingen, San Diego, Calif.). The controls are 10 µg of pcDNA-EPO and 10 µg of pcDNA 2.1(−).

EXAMPLE 2

EMPLIFICATION: PRODUCTION OF AN IL-2-FasL FUSION PROTEIN

Only certain leukemia or lymphoma cells, or recently activated T cells, bear the trimolecular high-affinity IL-2R (IL-2R is expressed as high, intermediate or low-affinity binding sites). The high affinity IL-2R is a specific marker of T cell activation, and is an inducible element responsible for enhancing the affinity of the IL-2R for IL-2 (Smith, 1989; Strom et al., 1993; Strom et al., 1992). The principle of using therapy directed against the high affinity IL-2R as a means of achieving selective immunosuppression and/or tolerance is well-established (Strom et al., 1992; Waldmann, 1993). With a number of problems of immunogenicity, suboptimal affinity, short circulating half-life, and inability to direct host cytolytic immune effector mechanisms against target cells the current high IL-2R targeting strategies, including monoclonal antibodies directed against the p55 chain of the IL-2R and IL-2/toxin fusion proteins, may impose limits on their clinical utility. These problems could be addressed by linking the IL-2 peptide to the the FasL peptide via the immunoglobin hinge region peptide.

The structure similarities of FasL with TNFa suggests that the FasL also exists as a trimer. Moreover, the anti-Fas antibody is an Ig M (Yonehara et al., 1989), a pentamer tending to not aggregate, whereas the anti-APO-1 antibody is an IgG3 (Trauth et al., 1989), which tends to aggregate. The F(ab)2 fragment of the anti-APO-1 antibody and its isotypes have little cytotoxic activity (Takeshita et al., 1992). However, these divalent anti-APO-1 antibodies induced apoptosis when they are cross-linked by second antibodies. These results indicate that dimerization of Fas is insufficient to transduce the apoptotic signal, and they are consistent with a trimeric structure for the Fas ligand. Therefore, the IL-2-FasL fusion protein requires target cells that express both high affinity IL-2R and Fas in order to induce apoptosis. This fusion protein would target only certain leukemia or lymphoma cells, or recently activated T cells which bear both high affinity IL-2R and Fas. Thus the target specificity is ensured by the dimerized form of this fusion protein. The FasL protein is a transmembrane protein where the ecto cellular portion is the C terminus end of the protein. This was considered in making the fusion protein described below.

CONSTRUCTION OF THE MURINE IL-2-FasL FUSION PROTEIN

The nucleotide sequences of wild type murine IL-2 and FasL can be obtained from Kashima, N., et al., Nature 313:402 (1985) and Takahashi, T., et al., Cell 76:969 (1994) respectively, each of which is herein incorporated by reference in its entirety. An IL-2-FasL fusion protein is constructed by linking a IL-2 cDNA and a FasL cDNA with a DNA strand encoding the hinge region polypeptide of murine IgG2a: GAGCCCAGAGGGCCCACACTCAAGC-CCTGTCCTCCATGCAAATGCCCA (SEQ ID NO. 29).

cDNA for murine IL-2 and FasL are generated from mRNA extracted from Con A stimulated murine splenic cells (C57BL/6J: The Jackson Laboratory, Bar Harbor, Me.) in a standard technique using reverse transcriptase MMLV-RT (Gibco BRL, Grand Island, N.Y.) with a synthetic oligo-dT (12–18) oligonucleotide (Gibco BRL). The IL-2 cDNA was then amplified by PCR using IL-2 specific synthetic oligonucleotides. The 5' oligonucleotide inserts a unique Not I restriction site 51 nucleotides 5' to the translational start codon, while the 3' oligonucleotide eliminates the termination codon and extend 18 nucleic acid sequence encoding the first 6 amino acid of hinge. By using two sequential PCR with synthetic 3' oligonucleotide 36 nucleic acid sequence encoding the last 12 amino acid of hinge were extended 3' to IL-2 sequence and insert a unique BglII restriction site 3' to the hinge. Synthetic oligonucleotides used for the amplification of the ecto-cellular domain cDNA of FasL change the first two codons from Gln and Leu to Asp and Pro to create a unique BamHI site spanning 5' end of ecto-cellular domain of FasL and introduce a unique Xba I site 3' to the termination codon. Primers used to produce murine IL-2 and hinge are as follows: 5'-ATAGGCCGCTAATCACTCCT-CAGTGA (SEQ ID NO: 30), 3'-ACACCCGGGAGACCCGAGGACTCCCGAACAA-CTCTACTA (SEQ ID NO: 31), 3'-ACCCTCCT- GTC-CCGAACTAACACCCGGGAGACCCGAGGAC (SEQ ID NO: 32), 3'-ATCCTAGACCCGTAAACGTACCTCCTG-TCCCGAACTAACAC (SEQ ID NO: 33). Primer used to produce murein FasL are as follows: 5'-ATGGATCCCTTCCACCTGCAGAAGG (SEQ ID NO: 34), 3'-GCAGATCTGAATTTCGAATATGTTCG (SEQ ID NO: 35).

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A fusion protein comprising an IL-2 protein and a FasL protein covalently linked a peptide comprising at least one immunoglobulin hinge region amino acid sequence.

2. The fusion protein of claim 1, wherin the immunoglobulin hinge region is the $IgG_{2A}$ hinge region.

3. The fusion protein of claim 2, wherein the $IgG_{2A}$ hinge region comprises SEQ ID NO: 19, 20, or 21.

4. The fusion protein of claim 1, wherein the immunoglobulin hinge region is the human $IgG_1$ hinge region.

5. The fusion protein of claim 4, wherein the $IgG_1$ hinge region comprises SEQ ID NO: 1, 2, or 3.

6. The fusion protein of claim 1, wherein the immunoglobulin hinge region is the mouse $IgG_1$ hinge region.

7. The fusion protein of claim 6, wherein the $IgG_1$ hinge region comprises SEQ ID NO: 16, 17, or 18.

8. The fusion protein of claim 1, wherein the immunoglobulin hinge region is the $IgG_3$ hinge region.

9. The fusion protein of claim 8, wherein the $IgG_3$ hinge region comprises SEQ ID NO: 6, 7, or 9.

10. An isolated nucleic acid comprising a nucleotide sequence which encodes the fusion protein of claim 1.

11. A vector comprising the nucleic acid of claim 10.

12. A host cell transfected with the vector of claim 11.

13. A pharmaceutical composition comprising a therapeutically effective amount of the fusion protein of claim 1 and a pharmaceutically acceptable carrier.

14. The fusion protein of claim 1 having a formula selected from the group consisting of IL-2-hinge region-FasL; FasL-hinge region-IL2; IL2-hinge region-hinge region-FasL; or FasL-hinge region-hinge region-IL2.

15. A fusion protein comprising an IL-2 protein and a FasL protein covalently linked by an immunoglobulin hinge region wherein the immunoglobulin hinge region is selected from the group consisting of $IgG_1$, $IgG_{2A}$ or $IgG_3$.

16. The fusion protein of claim 15, wherein the immunoglobulin hinge region comprises SEQ ID NO: 1, 2, or 3.

17. The fusion protein of claim 15, wherein the immunoglobulin hinge region comprises SEQ ID NO: 19, 20, or 21.

18. The fusion protein of claim 15, wherein the immunoglobulin hinge region comprises SEQ ID NO: 16, 17, or 18.

19. The fusion protein of claim 15, wherein the immunoglobulin hinge region comprises SEQ ID NO: 6, 7, or 8.

20. A method for producing a fusion protein comprising an IL-2 protein and a FasL protein covalently linked by at least one immunoglobulin hinge region amino acid sequence comprising:

a) transfecting a host cell with a vector comprising a nucleic acid comprising a nucleotide sequence which encodes the fusion protein comprising an IL-2 protein and a FasL protein covalently linked by at least one immunoglobulin hinge region amino acid sequence; and b) culturing the host cell in a suitable medium to produce the fusion protein.

* * * * *

UNITED STATES PATENT AND TRADEMARK OFFICE
CERTIFICATE OF CORRECTION

PATENT NO. : 6,165,476
DATED : December 26, 2000
INVENTOR(S) : Terry B. Strom and Xin Xiao Zheng It is certified that error appears in the above-identified patent and that said Letters Patent is hereby corrected as shown below:

<u>Title page,</u>
Item [75], the name of inventor "Xin Xiao Zhen" should be corrected to read "Xin Xiao Zheng."

<u>Claim 1,</u>
Line 2, after "linked," insert -- by --.

Signed and Sealed this

Fourth Day of December, 2001

Attest:

*Nicholas P. Godici*

NICHOLAS P. GODICI
*Attesting Officer*   *Acting Director of the United States Patent and Trademark Office*